(12) United States Patent
Cho et al.

(10) Patent No.: US 11,529,064 B2
(45) Date of Patent: Dec. 20, 2022

(54) METHOD AND DEVICE FOR MEASURING BIOMETRIC SIGNAL BY USING RADAR

(71) Applicant: WRT LAB CO., LTD., Seoul (KR)

(72) Inventors: Sung Ho Cho, Seoul (KR); Jeong Woo Choi, Seoul (KR)

(73) Assignee: WRT LAB CO., LTD., Seoul (KR)

( * ) Notice: Subject to any disclaimer, the term of this patent is extended or adjusted under 35 U.S.C. 154(b) by 363 days.

(21) Appl. No.: 16/480,101

(22) PCT Filed: Jan. 25, 2018

(86) PCT No.: PCT/KR2018/001137
§ 371 (c)(1),
(2) Date: Jul. 23, 2019

(87) PCT Pub. No.: WO2018/139881
PCT Pub. Date: Aug. 2, 2018

(65) Prior Publication Data
US 2019/0374126 A1 Dec. 12, 2019

(30) Foreign Application Priority Data

Jan. 26, 2017 (KR) .......................... 10-2017-0012513

(51) Int. Cl.
A61B 5/05 (2021.01)
A61B 5/00 (2006.01)
(Continued)

(52) U.S. Cl.
CPC ............. A61B 5/05 (2013.01); A61B 5/7203 (2013.01); A61B 5/7257 (2013.01); G01S 7/415 (2013.01);
(Continued)

(58) Field of Classification Search
None
See application file for complete search history.

(56) References Cited

U.S. PATENT DOCUMENTS

2012/0146796 A1* 6/2012 Margon ............... A61B 5/05
340/573.1
2015/0223733 A1* 8/2015 Al-Alusi ............... G01S 13/88
600/479

FOREIGN PATENT DOCUMENTS

JP 2016-135233 A 7/2016
KR 10-1145646 B1 5/2012
(Continued)

OTHER PUBLICATIONS

International Search Report issued in PCT/KR2018/001137, dated May 17, 2018.

Primary Examiner — Yi-Shan Yang
(74) Attorney, Agent, or Firm — Locke Lord LLP; Scott D. Wofsy; Gabrielle L. Gelozin

(57) ABSTRACT

Disclosed are a method and a device for measuring a biometric signal by using a radar. The disclosed method measures a plurality of biometric signals by using a radar by: (a) receiving the plurality of biometric signals from the radar; (b) calculating distance information of the received plurality of biometric signals and classifying the same on the basis of a distance; (c) selecting a signal having a largest variance according to a time; (d) further selecting a number of signals among signals having a distance with the signal selected in the step (c) smaller than an arbitrary distance from the distance-based classified signals; (e) converting all signals selected from a time domain to a frequency domain; (f) calculating a reliability of each biometric signal from the converted distance-based signals; and (g) detecting a corresponding biometric signal by selecting the distance-based signal where the calculated reliability is highest.

8 Claims, 5 Drawing Sheets

(51) Int. Cl.
    *G01S 7/41*          (2006.01)
    *A61B 5/024*       (2006.01)
    *A61B 5/08*         (2006.01)
    *G01S 13/02*       (2006.01)

(52) U.S. Cl.
    CPC ......... *A61B 5/02444* (2013.01); *A61B 5/0816* (2013.01); *G01S 13/0209* (2013.01)

(56) References Cited

FOREIGN PATENT DOCUMENTS

| | | |
|---|---|---|
| KR | 10-2014-0106795 A | 9/2014 |
| KR | 10-2015-0054368 A | 5/2015 |
| KR | 10-2015-0088135 A | 7/2015 |
| KR | 10-2016-0148904 A | 12/2016 |

\* cited by examiner

METHOD AND DEVICE FOR MEASURING BIOMETRIC SIGNAL BY USING RADAR

CROSS REFERENCE TO RELATED APPLICATIONS

This application is a U.S. National Phase Application filed under 35 U.S.C. § 371, based on International PCT Patent Application No. PCT/KR2018/001137, filed on Jan. 25, 2018, which application claims priority to Korean Patent Application No. 10-2017-0012513, filed on Jan. 26, 2017. The entire contents of these applications are incorporated herein by reference in their entirety.

TECHNICAL FIELD

The present invention relates to a method and device for measuring a biometric signal. More particularly, the present invention relates to a method and device for measuring a biometric signal by using a radar.

BACKGROUND ART

Recently, research and development of a bio-radar for detecting breathing and heartbeat signals in a non-contact manner is underway.

However, in case of a bio-radar, since a subject to be measured is the human body, radio frequency (RF) transmission signal power that can be radiated is severely limited. In addition, a signal received from the human body is very weak, and thus it is very vulnerable to noise and interference from the surroundings.

Accordingly, a technique is provided where an impulse-radio ultra wide band (IR-UWB) radar (hereinafter, referred as "UWB radar") is used to measure a bio-signal.

Herein, "ultra wide band (UWB)" is a radio technique that uses a frequency bandwidth of 500 MHz or more, or using a broadband frequency where a fractional bandwidth, which is defined as the signal bandwidth with respect to the center frequency, is 25% or more. The UWB is advantageous in range resolution, permeability, strong immunity against narrowband noise, and coexistence with other devices sharing a frequency.

A UWB radar is a radar on which such UWB technique is grafted on the radar, and can recognize surrounding environments by transmitting an impulse signal having a short duration with a broadband characteristic in the frequency domain, and by receiving a signal that is reflected from an object or person.

Due to such characteristics of a UWB radar, research is being actively conducted to utilize UWB radar in various fields such as medical apparatuses for measuring a breathing rate and a heartbeat rate, portable radar apparatuses for rescuing people in a disaster scene, apparatuses for counting a number of people in a certain area, etc.

In an example, in Korean Patent Application Publication No. 10-2014-0106795, a "UWB-based contactless biometric signals tester" proposes a method of measuring a biometric signal of a breathing rate or heartbeat rage by using a UWB radar and providing a remote health management system by using the same.

In such a conventional technique, in order to extract each biometric signal from a radar signal, each biometric signal is extracted by determining a signal where a reliability is the highest among biometric signals generated in various points. Herein, each biometric signal is mainly extracted on the basis of a signal at a point where a variance according to a time is largest. However, each biometric signal has different frequency band, and when a breathing signal and a heartbeat signal are included at the same time, a signal variance is greatly affected by the breathing signal that is a relatively low frequency band, and the same is greatly affected by the heartbeat signal. Accordingly, a reliability of each biometric signal is not ensured by using a conventional method. Particularly, ensuring a reliability of a heartbeat signal that is a relatively high frequency band is difficult.

DISCLOSURE

Technical Problem

Accordingly, the present invention has been made keeping in mind the above problems occurring in the prior art, and an object of the present invention is to provide a method and device for measuring a biometric signal, the method and device being capable of accurately detecting each biometric signal from a plurality of biometric signals.

Technical Solution

In order to accomplish the above object, the present invention provides a method of measuring a biometric signal by using a radar, wherein the method measures a first biometric signal and a second biometric signal by using the radar, the method including: (a) receiving a signal including the first biometric signal and the second biometric signal from the radar; (b) calculating distance information of the received signal and classifying the same on the basis of a distance; (c) selecting a signal having a largest variance according to a time among the distance-based signals classified in the step (b); (d) further selecting a number of signals among signals having a distance with the signal selected in the step (c) smaller than an arbitrary distance from the distance-based signals classified in the step (b); (e) converting all signals selected in the steps (c) and (d) from a time domain to a frequency domain; (f) calculating each reliability of the first biometric signal and the second biometric signal from the distance-based signals converted in the step (e); (g) measuring the first biometric signal from the distance-based signal where the reliability of the first biometric signal calculated in the step (f) is highest; and (h) detecting the second biometric signal from the distance-based signal where the reliability of the second biometric signal calculated in the step (f) is highest.

In the step (f), the reliability of the first biometric signal may be calculated by dividing a largest peak value by a second largest peak value in a frequency domain of the first biometric signal, and the reliability of the second biometric signal may be calculated by dividing a largest peak value by a second largest peak value in a frequency domain of the second biometric signal The frequency band of the first biometric signal may be lower than the frequency band of the second signal, and in the step (h), the second biometric signal may be measured by removing the first signal and a harmonic component of the first signal from the distance-based signal where the reliability of the second biometric signal which is calculated in the step (f) is highest.

In the step (e), fast Fourier transform may be used.

In addition, according to another embodiment of the present invention, there is provided a method of measuring a biometric signal by using a radar, the method measures a plurality of biometric signals by using the radar, the method including: a) receiving the plurality of biometric signals from the radar; (b) calculating distance information of the received plurality of biometric signals and classifying the same on the basis of a distance; (c) selecting a signal having a largest variance according to a time among the distance-based signals classified in the step (b); (d) further selecting a number of signals among signals having a distance with the signal selected in the step (c) smaller than an arbitrary distance from the distance-based signals classified in the step (b); (e) converting all signals selected in the steps (c) and (d) from a time domain to a frequency domain; (f) calculating a reliability of each biometric signal from the distance-based signals converted in the step (e); and (g) detecting a corresponding biometric signal by selecting the distance-based signal where the reliability calculated in the step (f) is highest In the step (f), the reliability of each biometric signal may be calculated by dividing a largest peak value by a second largest peak value in a frequency domain of each biometric signal in the distance-based signals converted in the step (e)

In the step (g), a biometric signal to be detected may be detected by removing all biometric signals of a frequency band lower than the biometric signal to be detected and a harmonic component of all biometric signals of the frequency band lower than the biometric signal to be detected.

In the step (e), fast Fourier transform may be used.

In addition, according to still another embodiment of the present invention, there is provided a device for measuring a biometric signal by using a radar, the device measures a plurality of biometric signals by using the radar, the device including: a signal obtaining unit receiving the plurality of biometric signals from the radar; a distance calculating unit calculating distance information of the plurality of biometric signals obtained in the signal obtaining unit; a signal classifying unit classifying the plurality of biometric signals on the basis of a distance; a signal extracting unit selecting signals having a large variance among the distance-based classified signals; a signal converting unit converting the selected distance-based signals from a time domain to a frequency domain; a reliability calculating unit calculating a reliability of each biometric signal from the distance-based signals converted; and a biometric signal detecting unit detecting a corresponding biometric signal from the distance-based signal where the reliability calculated for each biometric signal is highest The reliability calculating unit may calculate the reliability of each biometric signal by dividing a largest peak value by a second largest peak value in a frequency domain of each biometric signal in the distance-based signals.

The device further includes: a signal removing unit removing biometric signals of a frequency band lower than the corresponding biometric signal and a harmonic component of the biometric signals of the frequency band lower than the corresponding biometric signal from the distance-based signal where the reliability calculated for each biometric signal is highest, wherein the signal detecting unit may detect the corresponding biometric signal from the signal from which the biometric signals of the frequency band lower than the corresponding biometric signal and the harmonic component of the biometric signals of the frequency band lower than the corresponding biometric signal are removed.

The signal converting unit may use fast Fourier transform.

The signal extracting unit may select a signal having a largest variance according to a time, and a number of signals among signals having a distance with the signal having the largest variance smaller than an arbitrary distance.

Advantageous Effects

As described above, the present invention can accurately detect each biometric signal from a plurality of biometric signals.

DESCRIPTION OF DRAWINGS

FIG. 1 is a flowchart showing a time flow of performing a biometric signal measuring method using a radar according to a preferred embodiment of the present invention.

MODE FOR INVENTION

Figure 1:
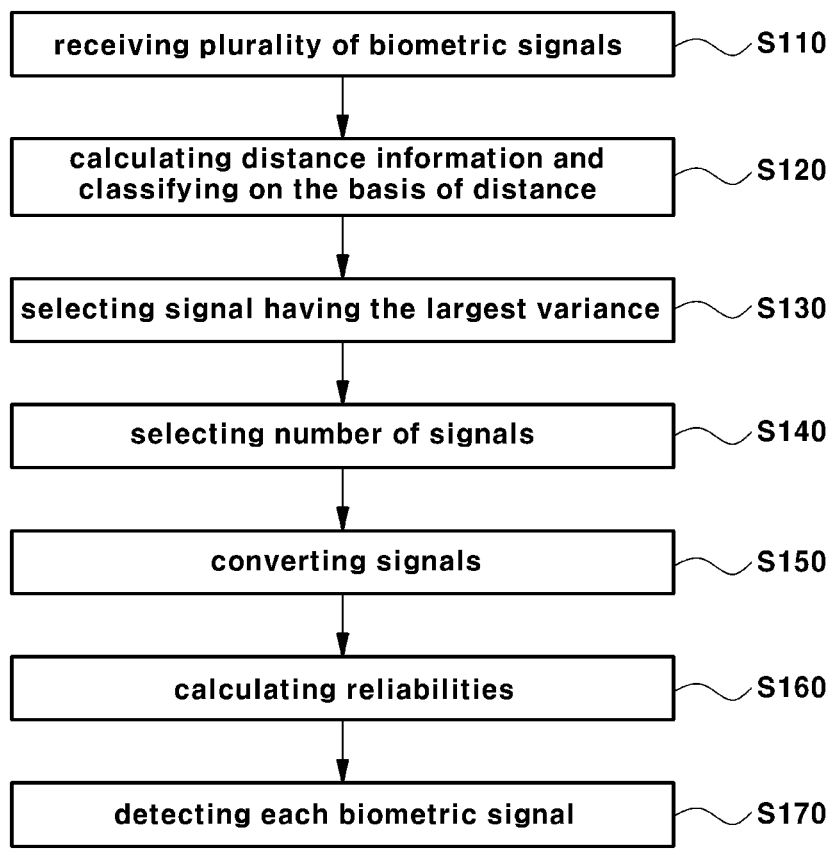
FIG. 1 is

While the invention is susceptible to various modifications and alternative forms, specific embodiments thereof are shown by way of example in the drawings and will herein be described in detail. However, this is not intended to limit the present invention to specific embodiments, and the present invention should be construed to encompass various changes, equivalents, and substitutions within the technical scope and spirit of the invention. Like numbers refer to like elements throughout in the description of each drawing.

Terms such as first, second, and the like may be used to describe various components and the components should not be limited by the terms. The terms are used only to discriminate one constituent element from another component. For example, a first component may be referred to as a second component, and similarly, the second component may be referred to as the first component without departing from the scope of the present invention. Hereinafter, detailed exemplary embodiments of the present invention will be described with reference to the accompanying drawings.

FIG. 1 is a flowchart showing a time flow of performing a biometric signal measuring method using a radar according to a preferred embodiment of the present invention.

Referring to FIG. 1, a biometric signal measuring method using a radar according to a preferred embodiment of the present invention may include: S110 of receiving a plurality of biometric signals; S120 of calculating and classifying distance information; S130 of selecting a signal having the largest variance; S140 of selecting a number of signals; S150 of converting the signals; S160 of calculating a reliability; and S170 of detecting each biometric signal.

S110 of receiving a plurality of biometric signals is receiving a plurality of biometric signals from a radar.

In the present invention, in an example, the radar may be an impulse-radio ultra wide band (IR-UWB) radar. Of course, a radar of the present invention is not limited to an IR-UWB radar, according to an embodiment, various radars capable of measuring a biometric signal from a subject to be measured may be used.

In an embodiment of the present invention, an example will be described where a breathing signal and a heartbeat signal are detected when a radar signal is transmitted to a subject to be measured, and a signal reflected from the subject to be measured includes a plurality of biometric signals including a breathing signal and a heartbeat signal. However, biometric signals of a subject to be measured which are measured by using the present invention include various signals such as breathing, heartbeat and muscle relaxation and contraction signals. Accordingly, a received signal may be a plurality of biometric signals including all of the above biometric signals.

S120 of calculating and classifying distance information is calculating a signal distance from the plurality of biometric signals received in S110, and classifying the signals on the basis of a distance. As described above, the plurality of biometric signals received in S110 may be signals reflected from the subject to be measured, and thus a distance of a signal generated from each point of the subject to be measured may be calculated, and the signals may be classified on the basis of a distance.

Figure 2:
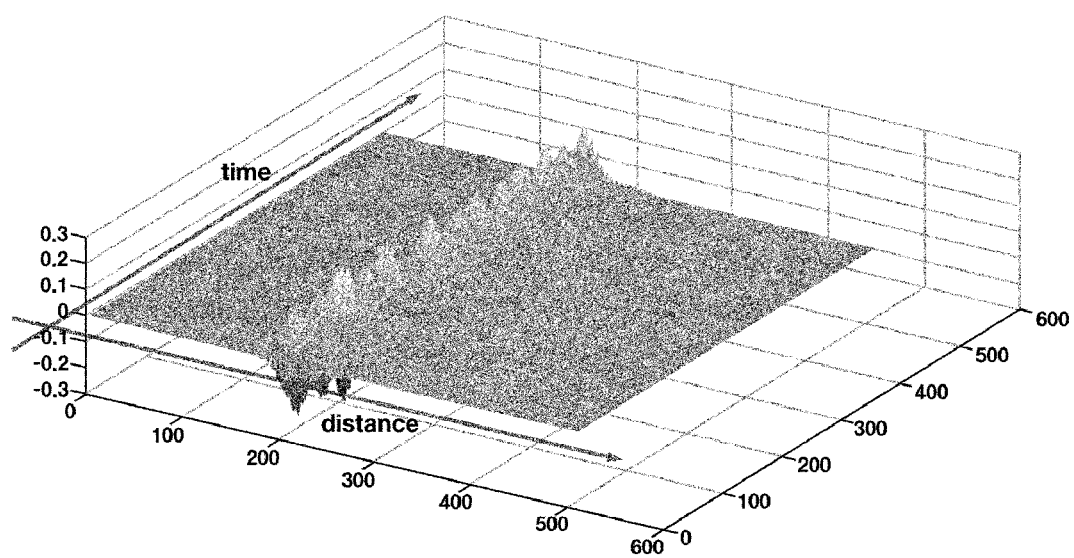
FIG. 2 is a view of a graph showing a plurality of received biometric signals as a function of a distance and a time.

FIG. 2 is a view of a graph showing a plurality of received biometric signals as a function of a distance and a time.

As shown in FIG. 2, a time from when a transmitted radar signal is reflected from the subject to be measured to when the reflected signal is arrived the radar may be measured, and the signal may be classified on the basis of a distance with the reflected point.

S130 of selecting a signal having the largest variance is selecting a signal having the largest variance according to a time among the plurality of distance-based classified biometric signals of S120.

Figure 3:
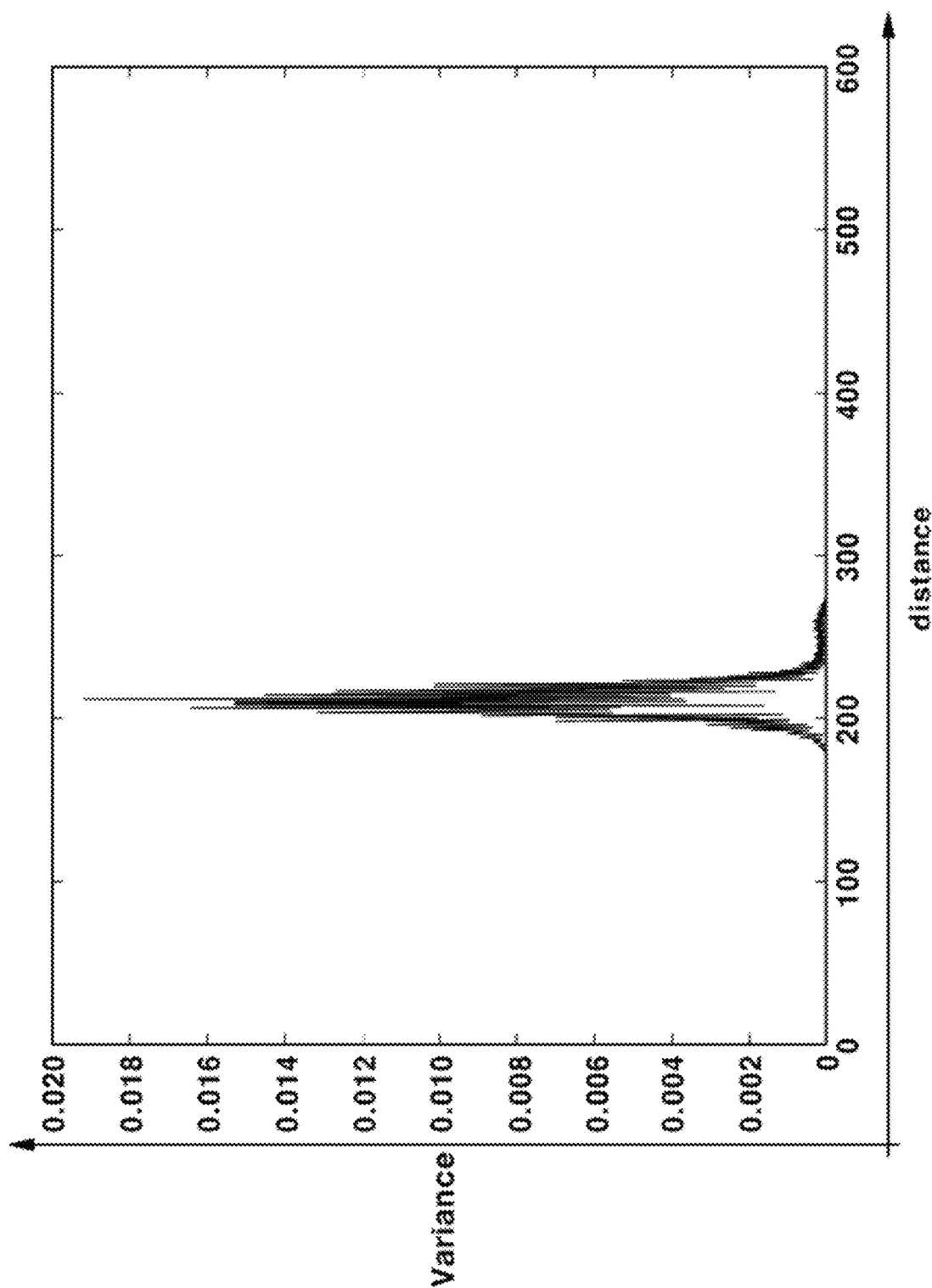
FIG. 3 is a view of a graph showing a variance of each distance-based signal as a function of a time.

FIG. 3 is a view of a graph showing a variance of each distance-based signal as a function of a time.

In an example of a graph of FIG. 3, a plurality of biometric signals reflected at a distance corresponding to a point where a variance value is maximum may be selected. Generally, a signal reflected at a point where such a variance value is maximum may be estimated as a signal with a high reliability. However, reliabilities of all signals included in the plurality of biometric signals are not high in signals having the largest variance value, and thus a distance in association with the highest reliability may vary for each biometric signal. Accordingly, the biometric signal measuring method using the radar according to a preferred embodiment of the present invention may further select another distance-based signal through S140.

S140 of selecting a number of signals is selecting larger number of distance-based signals on the basis of the distance-based signals selected in S130. As described above, a distance-based signal with a high reliability may be different for each biometric signal, and thus in S130, larger number of distance-based signals may be selected among signals present within an arbitrary distance with the selected distance-based signal.

Figure 4:
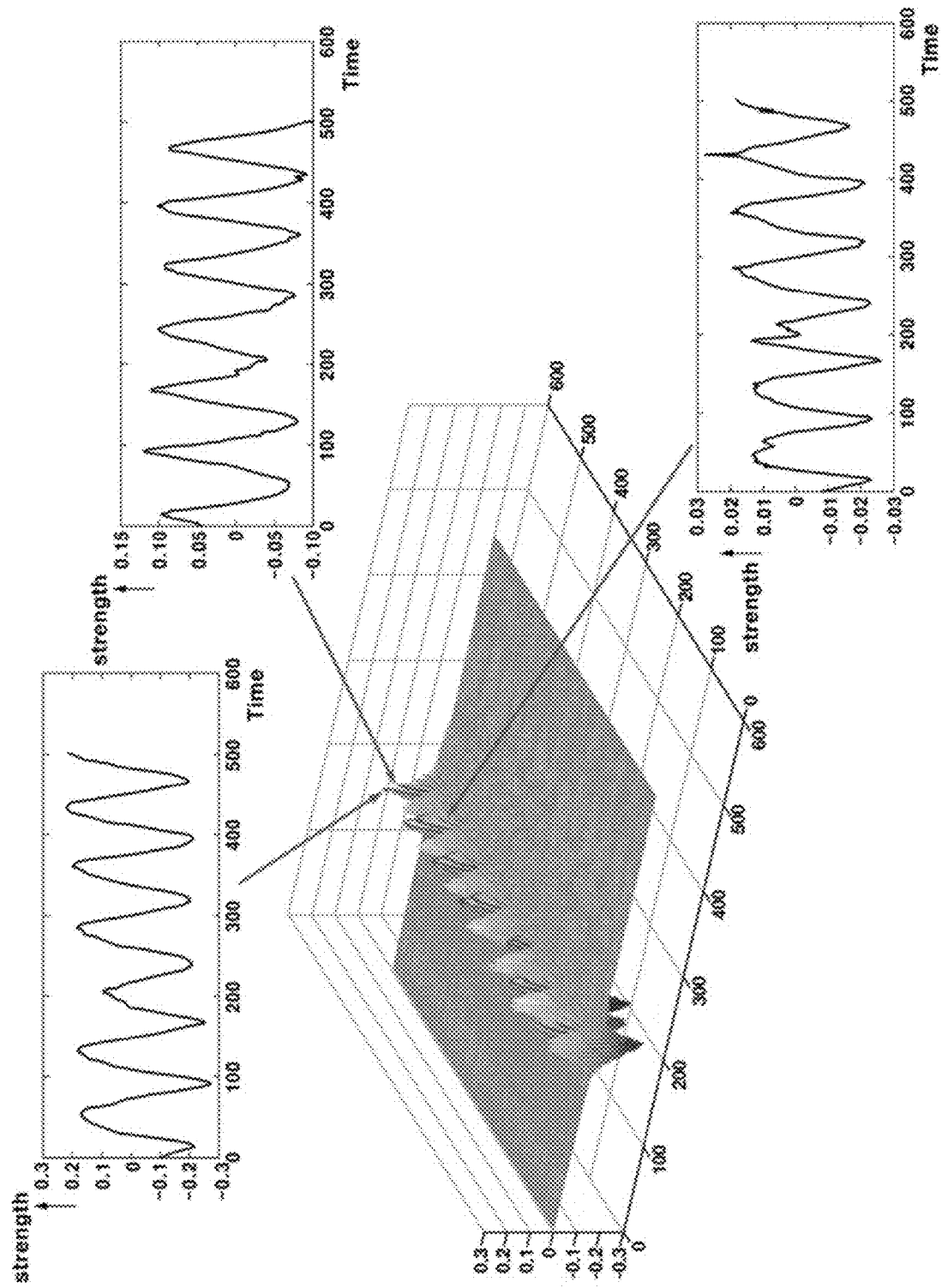
FIG. 4 is a view showing an example of performing S130 and S140 in the graph of FIG. 2.

FIG. 4 is a view showing an example of performing S130 and S140 in the graph of FIG. 2.

Referring to FIG. 4, in S130, with reference to the graph showing the variance in FIG. 3, based on the selected distance-based signal, larger distance-based signals may be arbitrarily selected according to a certain distance.

Herein, the signals may be converted to measure how much the selected distance-based signals have an actual reliability for each biometric signal.

S150 of converting the signals is converting the distance-based signals selected in S130 and S140 from a time domain to a frequency domain. Each biometric signal has different frequency band, and thus when the selected distance-based signals are converted into a frequency domain, a reliability of each biometric signal and the corresponding signal may be easily detected from the plurality of biometric signals.

Such a signal conversion may be performed by using fast Fourier transform (FFT).

S160 of calculating a reliability is calculating a reliability of each biometric signal from distance-based signals which are converted into a frequency domain in S150. In an embodiment of the present invention, a breathing signal and a heartbeat signal are detected as an example.

Figure 5:
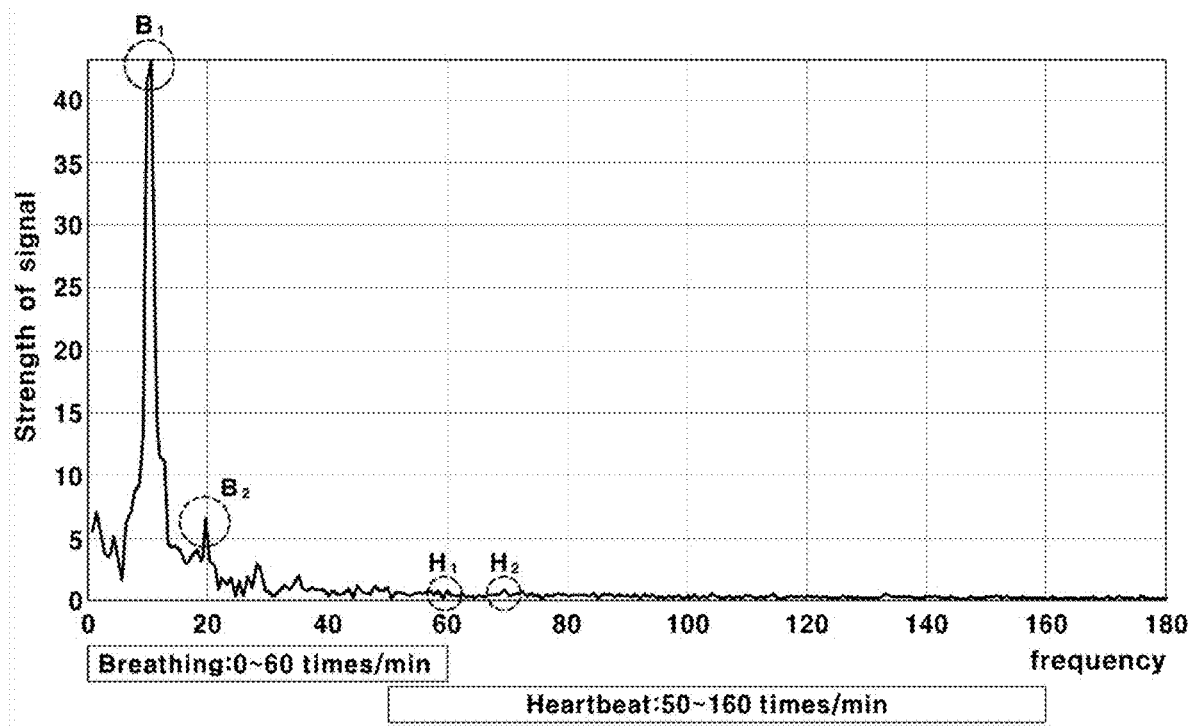
FIG. 5 is a view showing a method of calculating a reliability of a breathing signal and a heartbeat signal in a biometric signal of a frequency domain.

FIG. 5 is a view showing a method of calculating a reliability of a breathing signal and a heartbeat signal in a biometric signal of a frequency domain.

Referring to FIG. 5, a frequency band of a breathing signal is 0~60 times/min, and a frequency band of a heartbeat signal is 50~160 times/min. A reliability of each biometric signal may be calculated by taking into account of a frequency band of each biometric signal.

An equation for calculating a reliability R of each biometric signal is as the equation below.

$$R = P_1/P_2 \qquad [\text{Equation 1}]$$

In Equation 1, $P_1$ is the largest peak value in a frequency band of a corresponding biometric signal, and $P_2$ is the second largest peak value in a frequency band of a corresponding biometric signal.

Accordingly, in a graph showing a biometric signal of a frequency domain of FIG. 5, a reliability of a breathing signal may be calculated as $B_1/B_2$, and a reliability of a heartbeat signal may be calculated as $H_1/H_2$.

Herein, for all signals converted in S150, a reliability of each biometric signal may be calculated.

S170 of detecting each biometric signal is detecting a corresponding biometric signal in the distance-based signal with the highest reliability calculated in S160 for each biometric signal.

In a conventional method, all biometric signals are detected from a single signal having the largest variance, and thus a reliability of each biometric signal is not ensured. In the biometric signal measuring method using the radar according to a preferred embodiment of the present invention, in addition to a signal with the largest variance, a reliability of each biometric signal is measured from another signal, and thus an accurate biometric signal may be detected by detecting the corresponding biometric signal in a distance-based signal with the highest reliability for each biometric signal.

In an example, a reliability of a breathing signal may be highest in a distance-based signal with the largest variance, but a reliability of a heartbeat signal may be highest in a signal of another point rather than the distance-based signal with the largest variance. Accordingly, in the biometric signal measuring method using the radar according to a preferred embodiment of the present invention, a corresponding biometric signal may be detected in a distance-based signal with the highest reliability for each biometric signal.

In addition, motions due to breathing are relatively larger than motions due to heartbeat, and thus detecting a heartbeat signal is not easy due to a harmonic component and noise of a frequency component due to breathing. Particularly, a harmonic component has a significant size value by being added to external noise, and thus becomes an obstacle when detecting a heartbeat signal.

Accordingly, in detecting each biometric signal, when a biometric signal of a frequency band lower than the corresponding biometric signal is present, the corresponding biometric signal may be detected by removing the biometric signal of the frequency band lower than the corresponding biometric signal and a harmonic component of the biometric signal of the frequency band lower than the corresponding biometric signal from the distance-based signal with the highest reliability calculated in S160.

Figure 6:
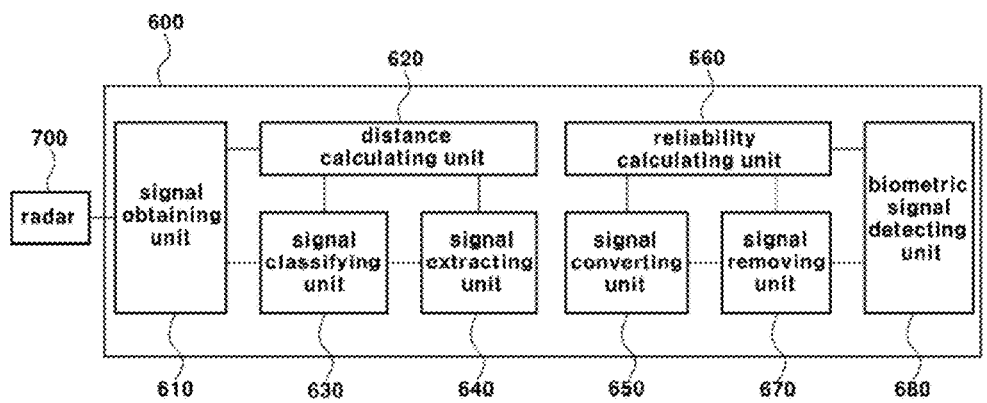
FIG. 6 is a view showing a structure of a biometric signal measuring device using a radar according to a preferred embodiment of the present invention.

FIG. 6 is a view showing a structure of a biometric signal measuring device using a radar according to a preferred embodiment of the present invention.

Referring to FIG. 6, a biometric signal measuring device 600 using a radar according to a preferred embodiment of the present invention may include a signal obtaining unit 610, a distance calculating unit 620, a signal classifying unit 630, a signal extracting unit 640, a signal converting unit 650, a reliability calculating unit 660, a signal removing unit 670, and a biometric signal detecting unit 680.

The signal obtaining unit 610 may perform S110 of receiving a plurality of biometric signals from a radar 700.

The distance calculating unit 620 and the signal classifying unit 630 may perform S120. The distance calculating unit 620 calculates a distance between the radar and a point at which a signal is reflected from the plurality of biometric signals which are reflected signals, and the signal classifying unit 630 classifies the plurality of received biometric signals on the basis of the calculated distance.

The signal extracting unit 640 may perform S130 and S140. Among distance-based signals classified in the signal classifying unit 630, a number of signals is extracted among a distance-based signal with the largest variance according to a time and signals within a predetermined distance with the distance-based signal with the largest variance.

The signal converting 650 perform S150 of converting the plurality of distance-based biometric signals extracted in the signal extracting unit 640 from a time domain to a frequency domain. The signal converting unit 650 may convert the signals by using fast Fourier transform (FFT).

The reliability calculating unit 660 performs S160 of calculating a reliability of each distance-based signal for all distance-based signals which are converted in the signal converting unit 650. The reliability may be calculated by dividing the largest peak value by the second largest peak value in a frequency band of each biometric signal.

The signal removing unit 670 and the biometric signal detecting unit 680 perform S170. Each biometric signal may be detected from a distance-based signal with the highest reliability of the corresponding biometric signal which is calculated in the reliability calculating unit 660. Particularly, the signal removing unit 670 removes a biometric signal of a frequency band lower than a biometric signal to be detected and a harmonic component of the biometric signal of the frequency band lower than the biometric signal to be detected, and detects the corresponding biometric signal from the signal from which the biometric signal of the frequency band lower than the biometric signal to be detected and the harmonic component of the biometric signal of the frequency band lower than the biometric signal to be detected are removed in the signal removing unit 670.

Although the present invention has been described in terms of specific items such as detailed components as well as the limited embodiments and the drawings, they are only provided to help general understanding of the invention, and the present invention is not limited to the above embodiments. It will be appreciated by those skilled in the art that various modifications and changes may be made from the above description. Therefore, the spirit of the present invention shall not be limited to the above-described embodiments, and the entire scope of the appended claims and their equivalents will fall within the scope and spirit of the invention.

The invention claimed is:

1. A method of measuring a biometric signal by using a radar, wherein the method measures a first biometric signal and a second biometric signal by using the radar, the method comprising:

(a) receiving, from the radar, a plurality of biometric signals including the first biometric signal and the second biometric signal, the first biometric and second biometric signals being a reflected signal reflected from a respective reflection point;

(b) calculating a respective distance between the respective reflection point and the radar associated with each of the plurality of biometric signals, and classifying the plurality of biometric signals into multiple groups on the basis of the respective distances thus calculated;

(c) selecting biometric signals having a variance greater than a predeterminate variance as a function of time from the multiple groups of the plurality of biometric signals thus classified on the basis of the respective distance in the step (b);

(d) selecting, further, from the multiple groups of the plurality of biometric signals thus selected in the step (b), a number of biometric signals having respective calculated distances smaller than a predetermined distance associated with the biometric signal selected in the step (c);

(e) converting the selected biometric signals of step (c) and the selected biometric signals of step (d) from a time domain to a frequency domain;

(f) calculating a reliability of the first biometric signal and a reliability of the second biometric signal from the biometric signals converted in the step (e);

(g) determining the first biometric signal as a biometric signal having a highest reliability as calculated in the step (f) within a first frequency band; and (h) determining the second biometric signal as a biometric signal having a highest reliability as calculated in the step (f) within a second frequency band.

2. The method of claim 1, wherein in the step (f), the reliability of the first biometric signal is calculated by dividing a largest peak value by a second largest peak value in a frequency domain of the first biometric signal, and the reliability of the second biometric signal is calculated by dividing a largest peak value by a second largest peak value in the frequency domain of the second biometric signal.

3. The method of claim 2, wherein the first frequency band of the first biometric signal is lower than the second frequency band of the second biometric signal, and in the step (h), the second biometric signal is determined by removing the first biometric signal and removing a harmonic component thereof from the biometric signals converted in the step (e).

4. The method of claim 3, wherein in the step (e), fast Fourier transform is used.

5. A method of measuring a biometric signal by using a radar, the method measures a plurality of biometric signals by using the radar, the method comprising:

(a) receiving, from the radar, the plurality of biometric signals, the plurality of biometric signals being reflected signals reflected from a respective reflection point;

(b) calculating a respective distance between the respective reflection point and the radar associated with each of the plurality of biometric signals and classifying the plurality of biometric signals on the basis of the respective distances thus calculated;

(c) selecting a signal having a largest variance as a function of time from the plurality of biometric signals thus classified on the basis of the respective distance in the step (b);

(d) selecting, further, from the plurality of biometric signals thus selected in the step (b), a number of biometric signals having respective calculated distances smaller than a predetermined distance associated with the biometric signal selected in the step (c);

(e) converting the signal selected in step (c) and the number of signals selected in step (d) from a time domain to a frequency domain;

(f) calculating a respective reliability of each of the biometric signals converted in the step (e); and (g) detecting the respective reliability of a first biometric signal and a second biometric signal as the biometric signals having a reliability that is higher than the respective reliabilities of each of the biometric signals calculated in the step (f).

6. The method of claim 5, wherein in the step (f), the reliability of the first and the second biometric signals is calculated by dividing a largest peak value by a second largest peak value in the frequency domain of each biometric signal in the distance based signals converted in the step (e).

7. The method of claim 6, wherein in the step (g), detecting the respective reliability of the first biometric signal and the second biometric signal having the highest respective reliabilities among the reliabilities of each of the biometric signals calculated in the step (f) includes removing all biometric signals, within a frequency band lower than the first biometric signal and the second biometric signal, and their respective harmonic components.

8. The method of claim 7, wherein in the step (e), fast Fourier transform is used.

* * * * *